US011890040B2

(12) United States Patent
Little et al.

(10) Patent No.: US 11,890,040 B2
(45) Date of Patent: Feb. 6, 2024

(54) GUIDED GROWTH DEVICE AND METHOD

(71) Applicant: The Sydney Children's Hospitals Network (Randwick and Westmead) (incorporating the Royal Alexandra Hospital for Children), Westmead (AU)

(72) Inventors: David Graham Little, Westmead (AU); Yang Lu, Westmead (AU); Hannah Frances Mourney, Westmead (AU)

(73) Assignee: The Sydney Children's Hospitals Network (Randwick and Westmead) (incorporating the Royal Alexandra Hospital for Children), Westmead (AU)

( * ) Notice: Subject to any disclaimer, the term of this patent is extended or adjusted under 35 U.S.C. 154(b) by 173 days.

(21) Appl. No.: 17/309,454

(22) PCT Filed: Nov. 28, 2019

(86) PCT No.: PCT/AU2019/051305
§ 371 (c)(1),
(2) Date: May 27, 2021

(87) PCT Pub. No.: WO2020/107072
PCT Pub. Date: Jun. 4, 2020

(65) Prior Publication Data
US 2022/0071671 A1    Mar. 10, 2022

(30) Foreign Application Priority Data
Nov. 28, 2018    (AU) .............................. 2018904516

(51) Int. Cl.
*A61B 17/80*      (2006.01)
*A61B 17/70*      (2006.01)
(Continued)

(52) U.S. Cl.
CPC ...... *A61B 17/8004* (2013.01); *A61B 17/7059* (2013.01); *A61B 2017/00477* (2013.01); *A61B 2017/564* (2013.01)

(58) Field of Classification Search
CPC .................. A61B 17/7059; A61B 17/80–8095
See application file for complete search history.

(56) References Cited

U.S. PATENT DOCUMENTS 3,488,779 A  *  1/1970  Christensen ....... A61B 17/8071
                                                    606/71
5,827,286 A  *  10/1998  Incavo ............... A61B 17/8009
                                                    606/282
(Continued)

FOREIGN PATENT DOCUMENTS

CN      104873256      9/2015
CN      106539615      3/2017
(Continued)

OTHER PUBLICATIONS

International Search Report and Written Opinion for International Application No. PCT/AU2019/051305, dated Feb. 6, 2020, in 15 pages.
(Continued)

*Primary Examiner* — Eduardo C Robert
*Assistant Examiner* — Steven J Cotroneo
(74) *Attorney, Agent, or Firm* — Knobbe, Martens, Olson & Bear, LLP

(57) ABSTRACT

An orthopaedic device for securing between first and second regions of bone separated by a growth plate, the orthopaedic device comprising: a first portion to secure to a first fixing location on the first bone region; a second portion to secure to a second fixing location on the second bone region, the first fixing location and the second fixing location being laterally offset relative to a longitudinal axis of the bone; wherein the first and second portions are pivotally coupled (Continued)

between a first coupling location on the first portion and a second coupling location on the second portion such that movement of the first and second portions away from each other in a direction parallel to the longitudinal axis of the bone causes relative rotation of the first bone region and the second bone region thereby reducing the lateral offset of the first location and the second location.

44 Claims, 9 Drawing Sheets

(51) Int. Cl.
    *A61B 17/00*           (2006.01)
    *A61B 17/56*           (2006.01)

(56) References Cited

U.S. PATENT DOCUMENTS

| | | | |
|---|---|---|---|
| 6,514,274 B1* | 2/2003 | Boucher | A61B 17/0401 |
| | | | 606/232 |
| 7,857,837 B2* | 12/2010 | Lieponis | A61B 17/7059 |
| | | | 606/279 |
| 8,579,898 B2* | 11/2013 | Prandi | A61B 17/8061 |
| | | | 606/280 |
| 9,877,755 B2* | 1/2018 | Sampath | A61B 17/8023 |
| 9,956,015 B2* | 5/2018 | Ehmke | A61B 17/8057 |
| 10,076,375 B1 | 9/2018 | Martel | |
| 10,786,281 B2* | 9/2020 | Garcia | A61B 17/8085 |
| 11,457,965 B1* | 10/2022 | Evans | A61B 17/842 |
| 2006/0142767 A1* | 6/2006 | Green | A61B 17/80 |
| | | | 606/281 |
| 2006/0155279 A1* | 7/2006 | Ogilvie | A61B 17/7031 |
| | | | 606/328 |
| 2007/0093834 A1 | 4/2007 | Stevens et al. | |
| 2007/0299448 A1* | 12/2007 | Chin | A61B 17/7059 |
| | | | 606/276 |
| 2009/0275947 A1* | 11/2009 | Graham | A61B 17/8061 |
| | | | 606/280 |
| 2010/0114322 A1* | 5/2010 | Clifford | A61F 2/0811 |
| | | | 623/20.14 |
| 2012/0271358 A1* | 10/2012 | Stevens | A61B 17/68 |
| | | | 606/279 |
| 2014/0094851 A1* | 4/2014 | Gordon | A61B 17/7007 |
| | | | 606/264 |
| 2015/0032166 A1* | 1/2015 | Amato | A61B 17/808 |
| | | | 606/281 |
| 2015/0100090 A1* | 4/2015 | Burke | A61B 17/7059 |
| | | | 606/257 |
| 2015/0216565 A1* | 8/2015 | Paley | A61B 17/8061 |
| | | | 606/328 |
| 2015/0257803 A1 | 9/2015 | Sampath et al. | |
| 2017/0014143 A1 | 1/2017 | Dayton | |
| 2017/0252070 A1 | 9/2017 | Tacoa et al. | |
| 2018/0028242 A1 | 2/2018 | Parekh et al. | |

FOREIGN PATENT DOCUMENTS

| | | |
|---|---|---|
| EP | 3332721 A1 | 6/2018 |
| WO | WO 2008/005271 | 1/2008 |
| WO | WO 2010/144458 | 12/2010 |
| WO | WO 2013/029188 | 3/2013 |
| WO | WO 2016/123671 | 8/2016 |

OTHER PUBLICATIONS

Arami et al., Guiding Femoral Rotational Growth in an Animal Model, *The Journal of Bone & Joint Surgery*, Nov. 20, 2013, vol. 95, pp. 2022-2027.
Extended European Search Report in European Patent Application No. 19890072.2, dated Aug. 31, 2022, in 11 pages.

* cited by examiner

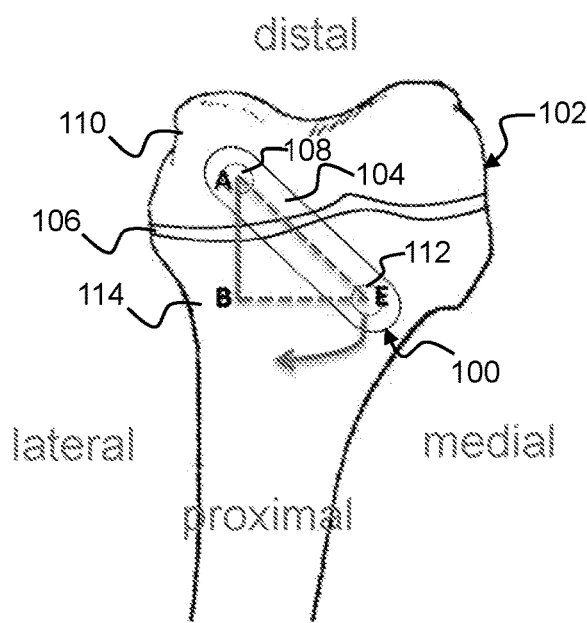
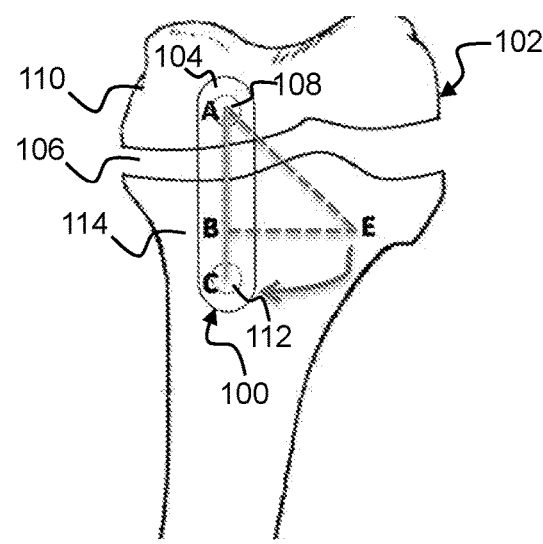
*Fig. 1A (prior art)*  *Fig. 1B (prior art)*

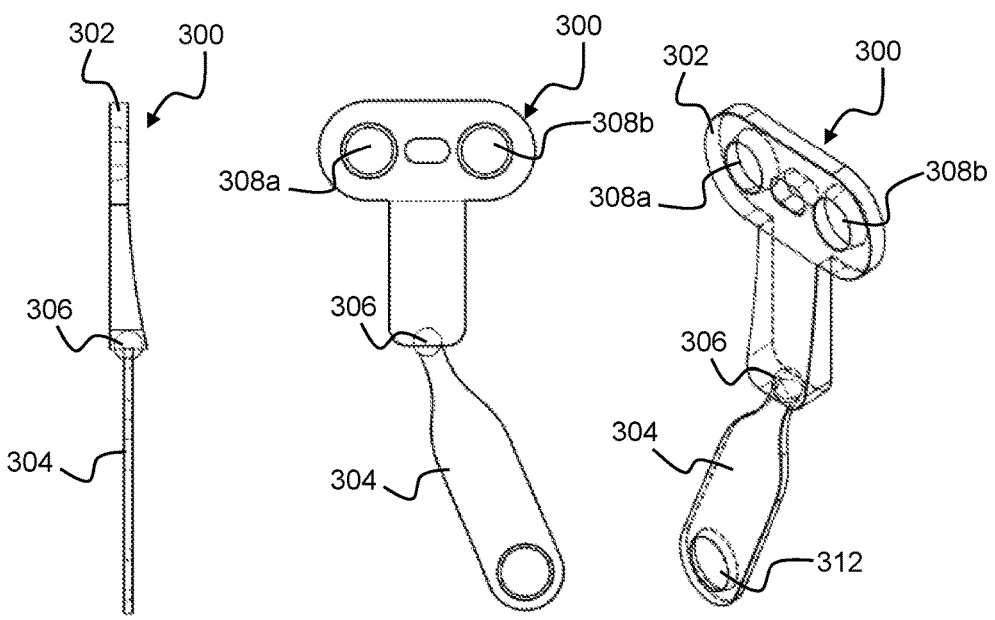
*Fig. 4A*  *Fig. 4B*  *Fig. 4C*
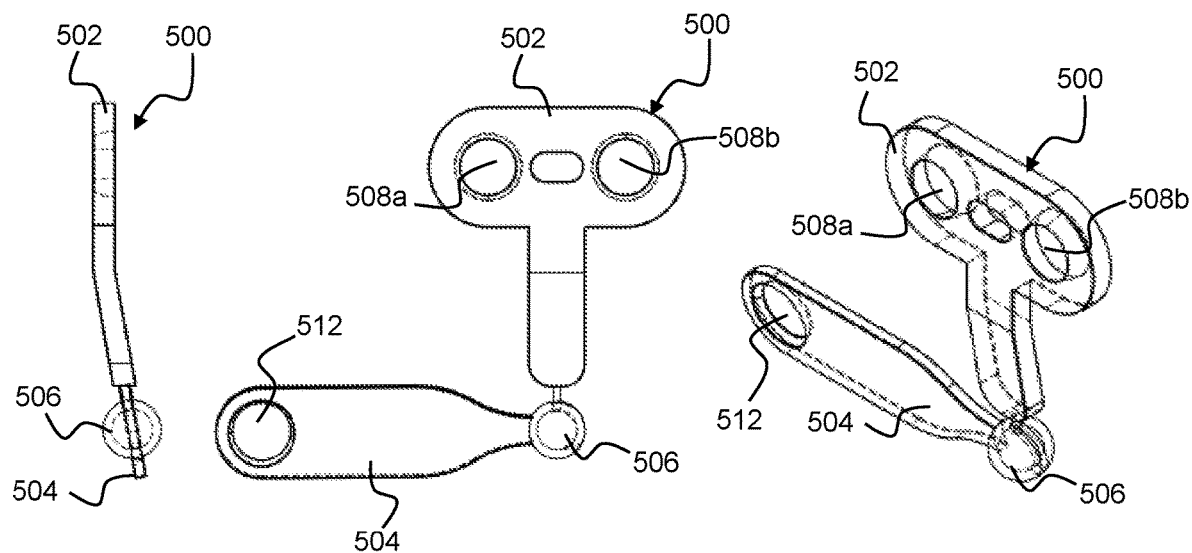
*Fig. 5A*  *Fig. 5B*  *Fig. 5C*

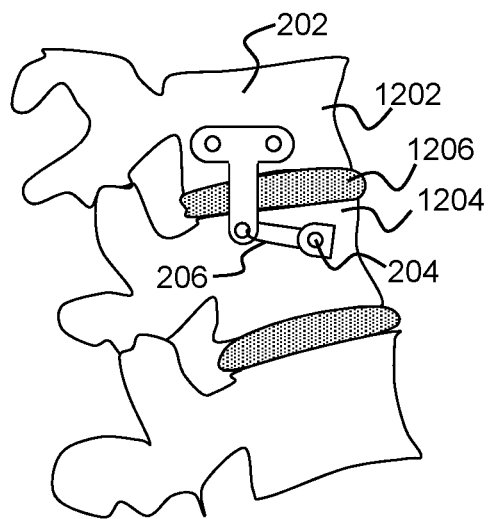 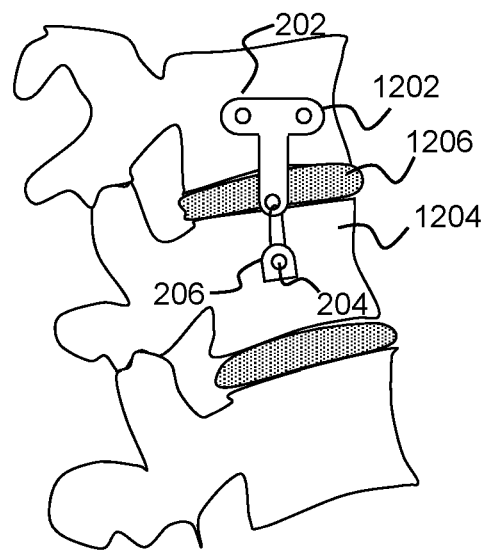
*Fig. 12A*         *Fig. 12B*
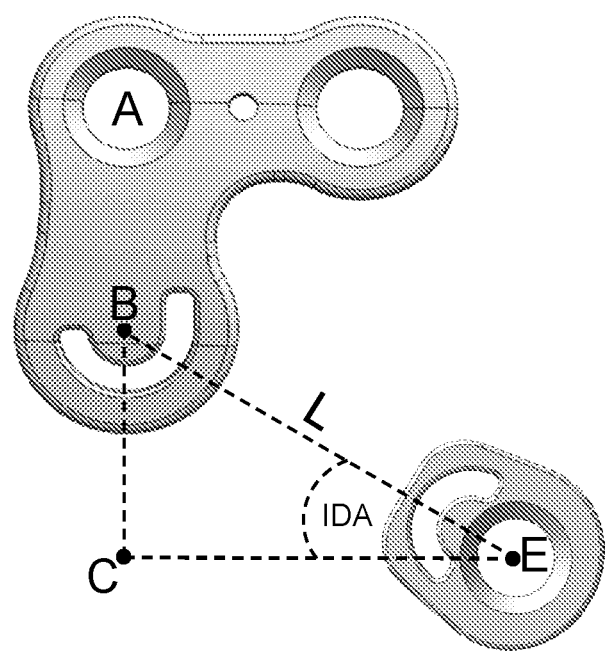
*Fig. 13*

GUIDED GROWTH DEVICE AND METHOD

CROSS-REFERENCE TO RELATED APPLICATIONS

This application is a U.S. National Phase under 35 U.S.C. § 371 of International Application No. PCT/AU2019/051305, filed Nov. 28, 2019, which claims priority to Australian Application Number 2018904516, filed Nov. 28, 2018.

TECHNICAL FIELD

The present disclosure relates to orthopaedic devices and methods for correction of deformities in bones, including deformities in bones at or adjacent a growth plate.

BACKGROUND

A growth plate, also known as the epiphyseal plate or physis, is a growing area of tissue adjacent to the diaphysis at each end of a long bone. The growth plate determines the future length and shape of the mature bone. The plate is found in growing children and adolescents. When growth is complete, the growth plate is replaced by an epiphyseal line of solid bone.

In some children, a growth plate will grow non-uniformly, with growth on one side of the growth plate being faster than on another side, causing an angular or a rotational deformity of the bone. Angular and rotational deformities may be congenital, caused by trauma or result from bone diseases. Rotational malalignment can be congenital, that is, present at birth. Neuromuscular disorders including cerebral palsy can also cause rotational and angular malalignment via abnormal muscle forces acting on the bone. Rotational malalignment can also be idiopathic, that is, of no known cause.

With rotational deformities, the most common current method of treatment involves subjecting the patient to an invasive osteotomy, whereby a region of the bone is cut and rotated to achieve re-alignment, typically about a joint, although in effect any section of the bone can be cut and rotated to achieve correction.

Rotational guided growth has been attempted by the use of non-orthogonal tension band plates (Arami Al, Bar-On E, Herman A, Velkes S, Heller S. Guiding femoral rotational growth in an animal model. *J Bone Joint Surg Am.* 2013 Nov. 20; 95 (22):2022-7). This method causes a torsional moment on the growth plate and effects a rotational deformity of the bones as the plates move from a non-orthogonal to an orthogonal position.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to a first aspect of the disclosure, there is provided an orthopaedic device for securing between first and second regions of bone separated by a growth plate, the orthopaedic device comprising: a first portion to secure to a first fixing location on the first bone region; a second portion to secure to a second fixing location on the second bone region; the first portion when secured to the first fixing location and the second portion when secured to the second fixing location being offset relative to a longitudinal axis of the bone; wherein the first and second portions are pivotally coupled between a first coupling location on the first portion and a second coupling location on the second portion such that movement of the first and second portions away from each other in a direction parallel to the longitudinal axis of the bone causes relative rotation of the first bone region to the second bone region thereby reducing the lateral offset of the first and second portions.

In some embodiments, movement of the first and second portions away from each other causes the orthopaedic device to move from a first configuration to a second, extended configuration.

In some embodiments, longitudinal growth of the bone causes the orthopaedic device to move towards the second, extended configuration.

The first coupling location may be offset relative to the first fixing location in a direction parallel to the longitudinal axis of the bone and towards the growth plate.

The first portion may extend at least partially and in some embodiments fully across the growth plate. Additionally or alternatively, the second portion may extend at least partially and in some embodiments fully across the growth plate.

The first coupling location may be provided on a part of the first portion extending at least partially across the growth plate. The second coupling location may be located on a part of the second portion extending at least partially across the growth plate.

The first portion may comprise a T-plate or an L-plate. The first portion may be shaped for local anatomy at which it is to be fixed. For example, the first portion may be configured to confirm to local anatomy.

In some embodiments, the first and second portions are pivotally coupled by a hinge. The hinge may be multiaxial. The hinge may comprise a ball and socket joint.

In some embodiments, the first portion comprises a post which interacts with a slot in the second portion to form the hinge. The post, may be slidable within the slot such that the distance between the second location and a centre of rotation of the hinge increases as the first and second portions are moved away from each other.

The orthopaedic device may further comprise means to limit rotation of the hinge until the distance between the second location and the centre of rotation of the hinge reaches a predetermined threshold. The means to limit rotation of the hinge may comprise a stop or bevel incorporated into the first portion.

The first and second portions may be pivotally coupled by a flexible link. The flexible link may comprise polyester tape. The flexible link may comprise one or more bands, loops, chains, tapes, strings, ropes, wires or the sutures. The flexible link may be manufactured from a material comprising stainless steel, polyester, polymer fibre, polyethylene, ultra-high molecular weight polyethylene (UHMWPE), silk, nylon, polyethylene terephthalate, polytetrafluoroethylene (PTFE), polyurethane, polypropylene, polyvinylidene fluoride, polydioxanone, or a combination thereof. The flexible link may form a continuous loop.

The first portion may comprises a first coupling slot for securing the link to the first portion at the first coupling location. The first coupling slot may be curved or arcuate. The first coupling slot may comprise a first open end for receiving the link. The second portion may comprise a second coupling slot for securing the link to the second portion at the second coupling location. The second coupling slot may be curved or arcuate. The second coupling slot may comprise a second open end for receiving the link. The distance between the first coupling location and the second coupling location may be between 20 and 30 mm, for example 25 mm.

In some embodiments, an inside surface of the first portion is contoured to match a surface of the first bone region. Additionally or alternatively, an inside surface of the second portion may be contoured to match a surface of the second bone region.

According to a another aspect of the disclosure, there is provided a system for correcting rotational deformity of first and second regions of bone separated by a growth plate, the system comprising two or more orthopaedic devices as described above, wherein the two or more orthopaedic devices are arranged around the circumference of the bone spaced equally from one another.

According to another aspect of the disclosure, there is provided a surgical guide for use with the orthopaedic device described above, the surgical guide comprising: a coupling configured to couple to first portion of the orthopaedic device in a predetermined relative orientation; and a surgical indicator configured to identify the second fixing location with the coupling coupled to the first portion in the predetermined relative orientation.

The surgical indicator may comprise a guide hole or the like. The guide hole may be used to guide drilling or tapping of screws for fixing the second portion to the bone.

In alternative embodiments, the surgical guide may be configured to couple to the second portion of the device instead of the first portion in a similar manner. In which case, the guide hole may be configured to guide securing of the first portion.

According to another aspect of the disclosure, there is provided a method of correcting a bone deformity using an orthopaedic device as described above, the method comprising: securing the first portion of the device to the first location on the first bone region; securing the second portion of the device to the second location on the second bone region.

The first and second portions of the device may be secured to the first and second locations such that an initial implantation angle between a first plane perpendicular to the longitudinal axis of the bone and a second plane intersecting the first coupling location and the second coupling location of between 25° and 35°, for example 30°.

The method may further comprise securing one or more additional orthopaedic devices between the first and second regions of the bone, the orthopaedic device and the one or more additional orthopaedic devices being equally spaced apart around the circumference of the bone so as to impart substantially equal relative rotational force on the first and second bone regions during growth of the bone in a direction parallel to the longitudinal axis of the bone.

The method may further comprise, after growth of the bone in a direction parallel to the longitudinal axis of the bone, removing or disabling one or more of the orthopaedic device and the one or more additional orthopaedic devices, the remaining orthopaedic device and/or one or more additional orthopaedic devices which have not been removed or disabled causing angular displacement of the first bone region relative to the second bone region to correct an angular deformity in the bone.

The bone may be the femur, the tibia, the fibula, the humerus, the ulna, or the radius of a human or animal. The bone may comprise a plurality of vertebrae.

Where the bone is a femur, the orthopaedic device is preferably secured on a lateral side or a medial side of the femur. Another orthopaedic device similar to the orthopaedic device may then be secured to the other of the lateral or medial side to which the first orthopaedic device is fixed to the femur.

Where the bone is a femur, the above method may correct femoral anteversion and antetorsion. Additionally, or alternatively, the first portion may be secured to the distal femoral epiphysis and the second portion fixed to the diaphysis of the distal femur relative to the distal femoral growth plate. Variations of the above method may correct femoral retroversion, internal tibial torsion, external tibial torsion, and any other rotational bone deformity.

At least the distal femoral epiphysis may be externally rotated relative to the distal femur.

According to another aspect of the disclosure, there is provided a spinal device for securing between first and second vertebra of a spine, the spinal device comprising: a first portion to secure to a first fixing location on the first vertebra; a second portion to secure to a second fixing location on the second vertebra, the first fixing location and the second fixing location being laterally offset relative to a longitudinal axis of the spine; wherein the first and second portions are pivotally coupled between a first coupling location on the first portion and a second coupling location on the second portion such that movement of the first and second portions away from each other in a direction parallel to the longitudinal axis of the bone causes relative rotation of the first vertebra and the second vertebra thereby reducing the lateral offset of the first location and the second location.

In some embodiments, the first coupling location is offset relative to the first fixing location in a direction parallel to the longitudinal axis of the spine. In some embodiments, the second coupling location is offset relative to the second fixing location in a direction parallel to the longitudinal axis of the spine.

In some embodiments, the first vertebra and the second vertebra are separated by two or more vertebral disc spaces.

According to another aspect of the disclosure, there is provided a guided growth system comprising a plurality of spinal devices as described above. In some embodiments, two or more spinal devices may be coupled between the first and second vertebra. In some embodiments, two or more spinal devices may each be coupled between a different pair of vertebra.

According to another aspect of the disclosure, there is provided a method of correcting a spinal deformity using a spinal device as described above, the method comprising: securing the first portion of the device to the first location on the first region on the vertebral bone; securing the second portion of the device to the second location on the second region on the vertebral bone.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

FIGS. 1A and 1B schematically illustrate an orthopaedic device known in the prior art;

FIGS. 4A, 4B and 4C schematically illustrate an orthopaedic device according to an embodiment of the present disclosure;

FIGS. 5A, 5B and 5C schematically illustrate an orthopaedic device according to an embodiment of the present disclosure;

FIGS. 12A and 12B show the orthopaedic device of FIGS. 2A and 2B secured between two vertebrae across a disc region of a subject;

FIG. 13 schematically illustrates the distance L and initial device angle (IDA) of the device shown in FIG. 11;

DETAILED DESCRIPTION

Figures 2A, 2B, 2C:
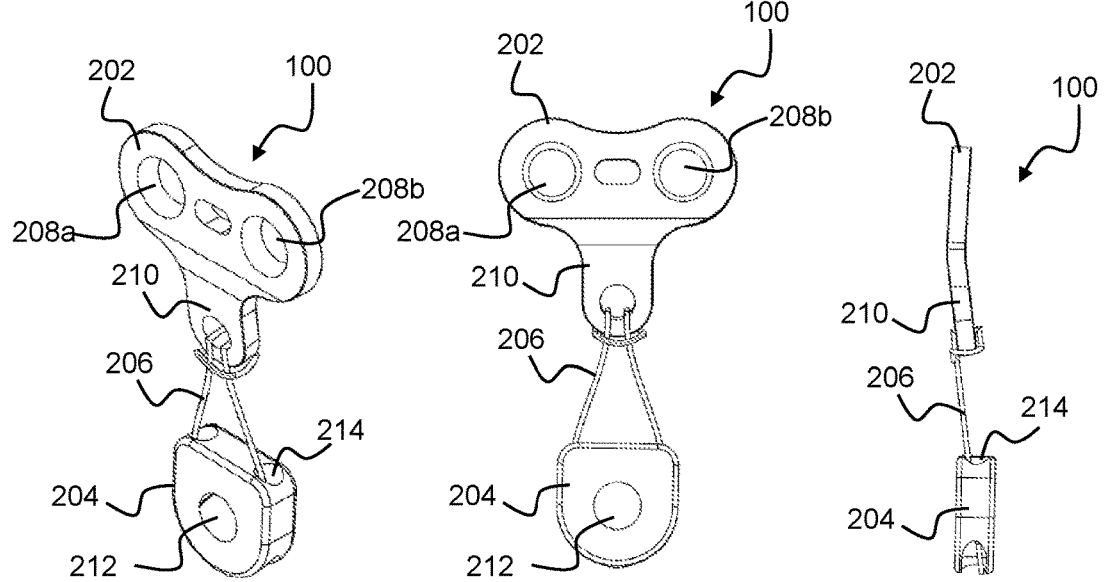
FIGS. 2A, 2B and 2C schematically illustrate an orthopaedic device according to an embodiment of the present disclosure.

FIGS. 1A and 1B schematically illustrate a state of the art orthopaedic device 100 for use in correcting a rotational abnormality in a femur 102 of a subject. FIG. 1A depicts the device 100 at the time of fixing to the femur 102. FIG. 1B depicts the device 100 after a duration of growth of the femur 102. Referring to FIG. 1A, the device 100 comprises a plate 104 fixed obliquely across a growth plate 106 of the femur 102 between a lateral location 108 on a distal region 110 of the femur 102 and a medial location 112 on a proximal region 114 of the femur 102, the distal and proximal regions 110, 114 being separated by the growth plate 106. The plate 104 may be fixed to the femur 102 using screws or nails (not shown) commonly used for fixation of known orthopaedic implants to bone. Whilst in FIGS. 1A and 1B the orthopaedic device 100 is shown fixed to the front of the femur 102, in other embodiments the orthopaedic device 100 may be fixed to a lateral or medial side of the femur 102.

As the bone grows in a direction parallel to the longitudinal axis of the femur 102, the device 100 (or combination of devices) imparts a torque on the distal region 110 of the femur 102 relative to the proximal region 114 which, in turn, causes the distal region 110 to rotate relative to the proximal region 114. This rotation continues during growth of the femur 102 until, as shown in FIG. 1B, the lateral location 108 and the medial location 112 are substantially aligned with one another in a direction parallel to the longitudinal axis of the femur 102.

The total longitudinal growth BC between the initial position of the device 100 shown in FIG. 1A and the final position of the device shown in FIG. 1B may be defined as follows:

$$BC = AE - AB$$

where AC=AE. For distances AB=20 mm and AE=28 mm, the total longitudinal growth allowed for by the device 100 can be calculated using the above formula as 8 mm. With the device causing a total relative rotation of the distal and proximal regions 110, 114 of 30°, this gives a rotation of 3.75° per millimetre of growth.

The prior art orthopaedic device 100 therefore has the ability to correct a rotational abnormality across a growth plate. However, the inventors have realised that there are some disadvantages associated with use of this device 100. Specifically, it has been found that the amount of rotation imparted by the device 100 per millimetre of growth of the bone 102 can lead to strain and even cause damage to the growth plate during longitudinal growth of the bone. Additionally, once the device 100 reaches its final position as shown in FIG. 1B, the bone is inhibited from growing any further in the direction parallel to the longitudinal axis of the bone. In many cases, the device 100 must then be removed at or prior to the device 100 reaching its final position as shown in FIG. 1B in order to prevent the device 100 from causing long term damage or further bone abnormalities.

Having regard to the drawbacks of the above described orthopaedic device 100, FIGS. 2A, 2B and 2C show perspective, front and side views of a novel orthopaedic device 200 according to an embodiment of the present disclosure. The device comprises a first portion 202 and a second portion 204 coupled by a flexible link 206.

The first portion 202 is in the shape of a T-plate and comprises a pair of fixing points 208a, 208b located at the top of the T for securing the first portion 202 to a first region of bone, and a securing point 210 at the base of the T for coupling the flexible link 206 thereto. Preferably, as shown best in FIG. 2C, the first portion 202 is contoured to match the surface of the first portion of bone to which the first portion 202 is to be secured. In the embodiment shown, the base of the T of the first portion 202 is bent away from the surface of the bone to avoid the first portion 202 from interfering with the growth plate as will become more evident in FIGS. 3A, 3B and 3C. In other embodiments, however, the first portion 202 and/or the second portion 204 may contour closer to the bone to reduce irritation to tissue surrounding the device 200. Preferably, however, the first portion 202 and/or the second portion 204 are contoured to protect the region between the first and second regions of bone.

The second portion 204 comprises a fixing point 212 for securing the second portion 204 to a second region of bone as well as one or more securing points 214 for coupling the flexible link 206 to the second portion 204.

The first portion 202, the second portion 204 or both may be malleable such that during surgery, a clinician is able to mould the device 200 to conform with the bone to which it is to be attached to and to ensure the device 200 does not interfere with the growth plate or other tissue around the bone. The first portion 202 and/or the second portion 204 of the device 200 (or any other device described herein) may be manufactures from aluminium, lead or similar malleable material to allow the clinician to mould the device 200 during surgery.

The flexible link 206 may comprise one or more bands, loops, chains, tapes, strings, ropes, wires or the sutures. The flexible link may be manufactured from stainless steel, polyester, polymer fibre (e.g. SuperCable®), polyethylene such as ultra-high molecular weight polyethylene (UHMWPE), silk, nylon, polyethylene terephthalate, polytetrafluoroethylene (PTFE), polyurethane, polypropylene, polyvinylidene fluoride, polydioxanone, or any combination thereof. Examples UHMWPE products include Dyneema® and FiberWire®, FiberWire® comprising a UHMWPE core with a braided jacket of polyester. The flexible link 206 may be continuous, forming a loop between the securing point 210 of the first portion 202 and the securing point 214 of the second portion 204.

Figures 3A, 3B, 3C:
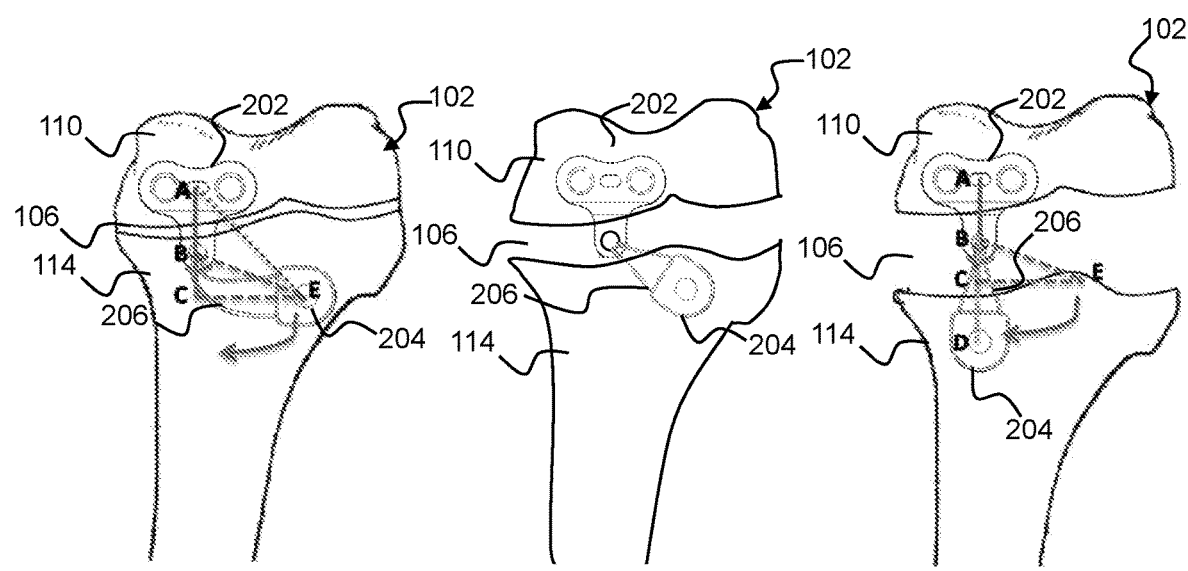
FIGS. 3A, 3B and 3C show the orthopaedic device of FIGS. 2A, 2B and 2C secured across a growth plate of a femur of a subject.

FIGS. 3A, 3B and 3C show the device 200 fixed to the femur 102 of a subject in a similar manner to the device 100 shown in FIGS. 1A and 1B. Like parts of the femur 102 have been denoted with like numbering. Whilst in FIGS. 3A, 3B and 3C the device 200 is shown fixed to the front of the femur 102, in other embodiments the device 200 may be fixed to a lateral or medial side of the femur 102. Where two devices 200 are provided, as described below in more detail, the two devices 200 may be positioned one on the lateral side and the other on the medial side of the femur 102.

FIG. 3A shows the configuration of the device 200 at the time of fixation to the femur. The first portion 202 of the device 200 is fixed at a lateral location on the distal portion 110 of the femur 102 and the second portion is fixed at a medial location on the proximal portion 114 of the femur 102 across the growth plate 106. The lateral and medial fixation sites are offset relative to the longitudinal axis of the femur 102. The first portion 202 is preferably fixed to the femur 102 such that it extends across the growth plate 106 with the securing point 210 situated on other side of the growth plate 106 to that to which it the first portion 202 is fixed. This prevents the flexible link 206 from interfering with the growth plate 106. In other embodiments, the device 200 may be attached to the bone such that second portion 204 extends across the growth plate 106, for similar reasons.

As the bone grows in a direction parallel to the longitudinal axis of the femur 102, tension in the flexible link 206 imparts a torque on the distal region 110 of the femur 102 relative to the proximal region 114 which, in turn, causes the distal region 110 to rotate relative to the proximal region 114 as shown in FIG. 3B.

The device 200 continues to apply torque during further longitudinal growth of the femur 102 until, as shown in FIG. 3C, the first and second portions 202, 204 are substantially aligned with one another in a direction parallel to the longitudinal axis of the femur 102.

It can be seen in this embodiment, as is the case in further embodiments described above, the securing point 210 is offset relative to the fixing points 208a, 208b in a direction parallel to the longitudinal axis of the bone and towards the growth plate. The flexible link 206 then provides a pivot about the securing point 210 which enables the distance between the fixation point on the proximal region 114 of the femur 102 and the fixation point on the distal region 110 of the femur 102 to increase during longitudinal growth of the femur 102. In other words, the provision of the pivot enables a greater amount of longitudinal growth per degree of rotation when compared to the oblique plate device 100 described with reference to FIGS. 1A and 1B, as evidenced by the following calculations.

Referring to FIGS. 3A and 3B, the total longitudinal growth of the femur 102—CD—between the initial position shown in FIG. 3A and the final position shown in FIG. 3C is as follows where BD=BE:

$$CD=BD-BC$$

Given the following dimensions of the device, AB=15 mm, BC=5 mm, AE=28 mm, BE=22.5 mm, and CD=20 mm, then the original positions of the fixing locations on the distal and proximal regions 110, 114 on the femur 102 for the device 200 are the same as those of the device 100 when secured to the femur 102. However, contrary to the device 100 shown in FIGS. 1A and 1B, the total longitudinal growth provided for by the device 200, as calculated by the above equation, is 17.5 mm when compared to 8 mm of longitudinal growth allowed by the prior art device 100. With the device imparting a relative total rotation of 30°, this gives a rotation of 1.7° per millimetre of growth.

Thus, the device 200 achieves more elongation per degree of rotation as compared to the prior art device 100 shown in FIGS. 1A and 1B. Thus, the strain placed on the growth plate by the device 200 is reduced when compared to the prior art device 100 and the bone 102 is able to grow by a greater length before removal of the device 200 is required.

In FIGS. 3A, 3B and 3C, a single orthopaedic device 200 is shown as being attached across the growth plate 106. This may be desirable where an angular deformity is present in the bone 102 as well as a rotational deformity, such as in conditions of bone dysplasia (e.g. Blunts) and in metabolic conditions (e.g. rickets). In such an embodiment, the rotational torque imparted by the device 200 may afford a desired degree of rotation and further also inhibit or slow the growth of the growth plate at one side relative to another side of the growth plate such that that the growth plate grows at a slower rate relative to the side opposite to which the device 200 is secured.

In some embodiments, however, angular correction may not be desired. In which case, two or more of the devices 200 may be secured across the growth plate 106, spaced equally apart from each other around the circumference of the femur 102. The devices 200 may then collectively impart a substantially uniform torque around the circumference of the femur 102 preventing potentially unwanted angular growth of the bone relative to its longitudinal axis. In such embodiments, the one of the two or more devices 200 may be positioned on a lateral side of the femur 102, and another of the two or more devices 200 may be positioned on a medial side of the femur 102.

In other embodiments, two or more devices 200 may be secured across the growth plate 106 until the desired rotational correction is achieved, for example when the first and second portions 202, 204 of each device 202 are laterally aligned. Then, having achieved the desired rotational correction, one or more of the two or more devices 200 may be removed or disabled (e.g. by removing the link between the first and second portions 202, 204) and if desired, a device or devices 200 may be left in place to correct an angular deformity, as a clinician sees fit.

FIGS. 4A, 4B and 4C show side, front and perspective views of another orthopaedic device 300 according to an embodiment of the present disclosure, which may be used in a similar manner to the device 200 described above.

The device comprises a first portion 302 and a second portion 304 coupled by a joint 306.

As with the device 200 described above, the first portion 302 of the device 300 is in the shape of a T-plate and comprises a pair of fixing points 308a, 308b located at the top of the T for securing the first portion 302 to a first portion of bone. As shown best in FIG. 4C, the first portion 302 is preferably contoured to match the surface of the first portion of bone to which the first portion 302 is to be secured. This contour comprises a taper towards the base of the T of the first portion 302. As well as providing a surface for mating with the bone surface, this taper also provides the requisite depth in the first portion 302 for elements of the joint 306 to be incorporated therein.

The second portion 304 comprises a fixing point 312 for securing the second portion 304 to a second portion of bone as well as one or more securing points 314 for coupling the flexible link 306 to the second portion 304.

As mentioned above, the first and second portions 302, 304 are coupled by the joint 306. The joint comprises a ball and socket arrangement which acts as a multi-axial hinge to enable the first and second portions 302, 304 to move in multiple axes about the joint 306.

In use, the device 300 acts in a similar manner to the device 200 described above. However, instead of the provision of the flexible link 206, the joint 306 provides the pivot between the first and second portions 302, 304. The combination of the first and second portions 302, 304 and the joint 306 allows the device 300 to extend further per degree of rotation as compared to the prior art device 100 shown in FIGS. 1A and 1B. As such, strain placed on the growth plate during correction is reduced when compared to the prior art device 100 and the bone is able to grow by a greater length before removal or disablement of the device 200 is required.

FIGS. 5A, 5B and 5C show a another device 500 which is a variation of the device 300 shown in FIGS. 4A, 4B and 4C. The device 500 comprises a first portion 502 and a second portion 504 coupled by a joint 506.

As with the device 300 described above, the first portion 502 of the device 500 is in the shape of a T-plate and comprises a pair of fixing points 508a, 508b located at the top of the T-plate for securing the first portion 502 to a first portion of bone. As shown best in FIG. 5C, the first portion 502 is preferably contoured to match the surface of the first portion of bone to which the first portion 502 is to be secured. To this end, the first portion 502 of the device 500 is bent away from the surface of the bone to avoid the first portion 502 from interfering with the growth plate 102 when secured thereacross.

The second portion 504 comprises a fixing point 512 for securing the second portion 504 to a second portion of bone as well as one or more securing points 514 for coupling the flexible link 506 to the second portion 504.

The joint 506, which couples the first and second portions 502, 504 together, comprises a ball and socket arrangement acting as a multi-axial hinge to enable the first and second portions 502, 504 to move in multiple axes relative to one another.

In use, the device 500 acts in a similar manner to the device 500 described above. However, instead of the provision of the joint 506 being integrated into the main body of the first portion 302, the joint 506 is provided distal to the first portion 502. This allows the distal end of the first portion 502 can have a reduced thickness relative to the device 300 shown in FIGS. 4A, 4B and 4C. This in turn may allow the distal end of the first portion 502 to be moulded or bent by a surgeon during surgery, for example to better confirm the first portion 502 to the bone to which the device 500 is mounted.

Figures 6A, 6B, 6C:
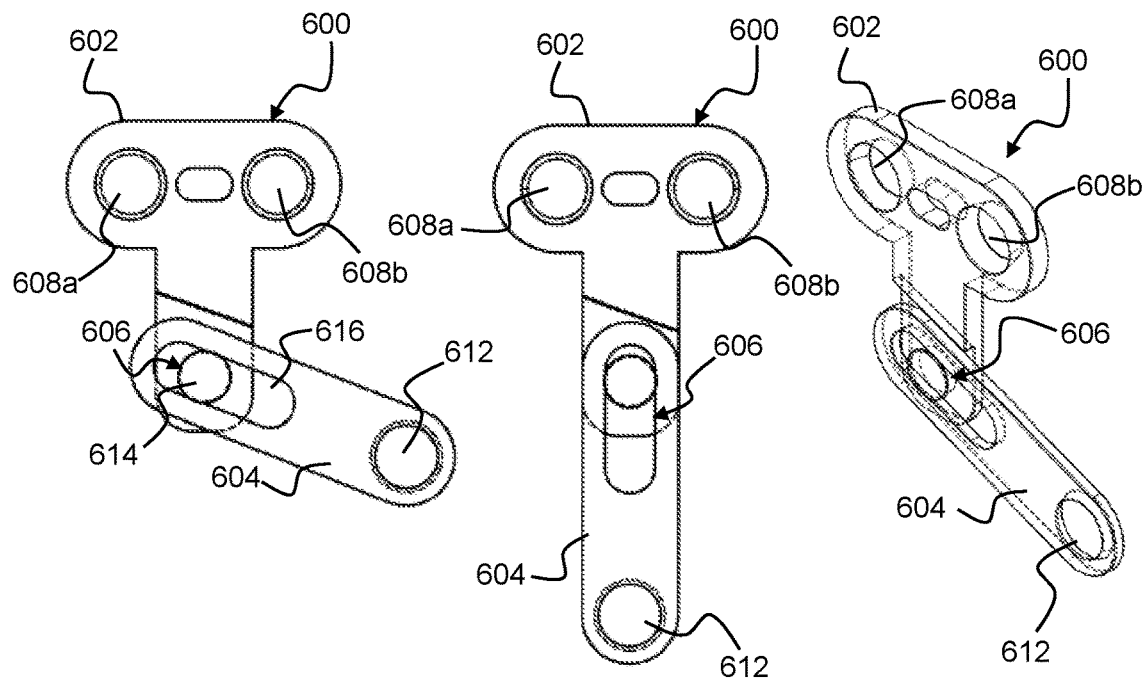
FIGS. 6A, 6B and 6C schematically illustrate an orthopaedic device according to an embodiment of the present disclosure.

FIGS. 6A, 6B and 6C show another orthopaedic device 600 which is a further variation of the device 300 shown in FIGS. 4A, 4B and 4C. The device 600 comprises a first portion 602 and a second portion 604 coupled by a joint 606.

As with the device 300 described above, the first portion 602 of the device 600 is in the shape of a T-plate and comprises a pair of fixing points 608a, 608b located at the top of the T-plate for securing the first portion 602 to a first portion of bone.

The second portion 604 comprises a fixing point 612 for securing the second portion 604 to a second portion of bone as well as one or more securing points 614 for coupling the flexible link 606 to the second portion 604.

The joint 606, which couples the first and second portions 602, 604 together, comprises a post 614 integrated into the first portion 602 which interacts with a slot 616 formed in the second portion 604. The post 614 is slidable within the slot 616 such that the distance between the fixing point 612 and the centre of rotation of the joint 606 can increase as the first and second portions 602, 604 move away from each other. Thus, the joint 606 allows for even more longitudinal extension per degree of rotation than the devices 200, 300 500 shown in the previous figures.

Figures 7A, 7B, 7C:
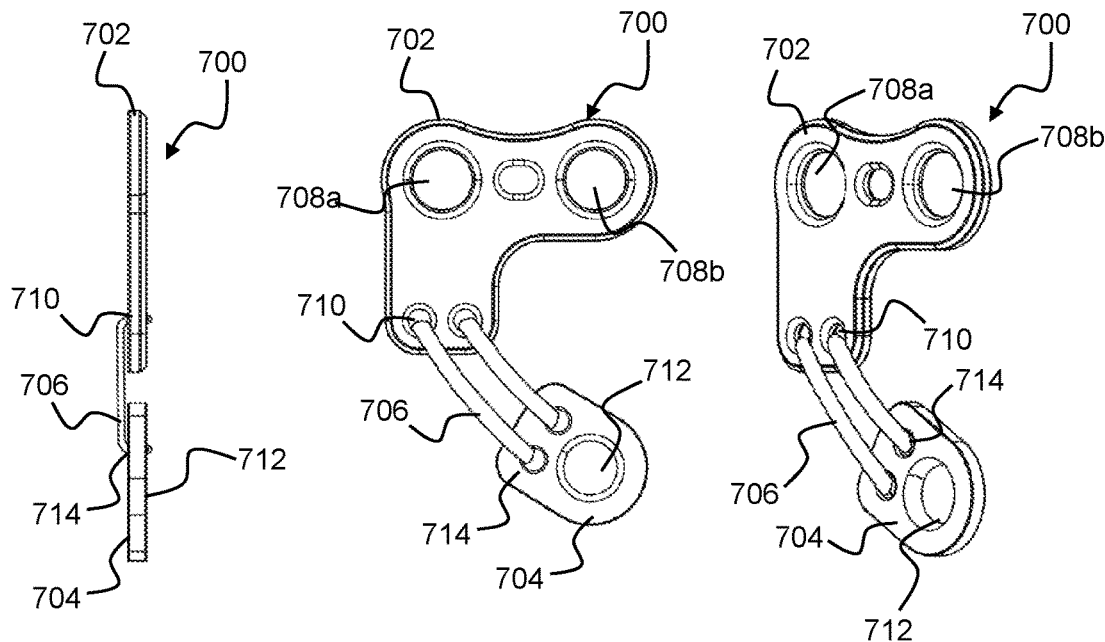
FIGS. 7A, 7B and 7C schematically illustrate an orthopaedic device according to an embodiment of the present disclosure.

FIGS. 7A, 7B and 7C show another orthopaedic device 700 which is a variation of the device 100 shown in FIGS. 2A, 2B and 2C. The device 700 comprises a first portion 702 and a second portion 704 coupled by a flexible link 706.

The first portion 702 is in the shape of an (inverted) L-plate and comprises a pair of fixing points 708a, 708b located at the base of the inverted L for securing the first portion 702 to a first region of bone, and a securing point 710 at the base of the inverted L for coupling the flexible link 706 thereto. As with the device 200 shown in FIG. 2, first portion 702 may be contoured to match the surface of the first portion of bone to which the first portion 702 is to be secured. In some embodiments, vertical of the T of the first portion 702 may bent away from the surface of the bone to avoid the first portion 702 from interfering with the growth plate. In other embodiments, the first portion 702 and/or the second portion 704 may contour closer to the bone to reduce irritation to tissue surrounding the device 700. Preferably, the first portion 702 and/or the second portion 704 are contoured to protect the region between the first and second regions of bone.

The second portion 704 comprises a fixing point 712 for securing the second portion 704 to a second region of bone as well as one or more securing points 714 for coupling the flexible link 706 to the second portion 704.

As with the device 200 of FIGS. 2A to 2C, the first portion 702, the second portion 704 or both may be malleable such that during surgery, a clinician is able to mould the device 700 to conform with the bone to which it is to be attached to and to ensure the device 700 does not interfere with the growth plate or other tissue around the bone.

The flexible link 706 may comprise one or more bands, loops, chains, tapes, strings, ropes, wires or the sutures and may be manufactured from the same materials as described above in respect of the flexible link 206 of the device 200 shown in FIGS. 2A to 2C. The flexible link 706 may also be continuous, forming a loop between the securing point 710 of the first portion 702 and the securing point 714 of the second portion 704.

The L-shaped device 700 is anatomically advantageous in that it is able to fit into spaces where other devices might not be able to fit. Additionally, the L-shaped device 700 provides less of a footprint, and requires a smaller incision during surgery for insertion under skin and muscle adjacent the bone. Further, the L-shaped device can provide the same rotational offset as the T-shaped device 200 but with a smaller footprint.

Figure 8:
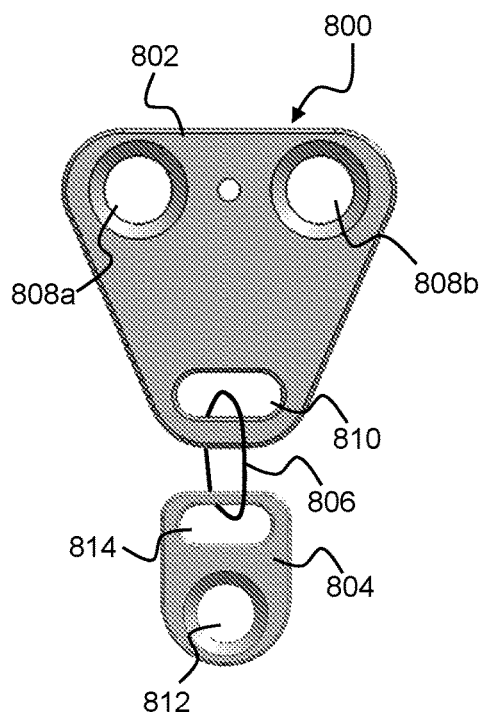
FIG. 8 schematically illustrates an orthopaedic device according to an embodiment of the present disclosure.

FIG. 8 shows another orthopaedic device 800 which is a variation of the device 100 shown in FIGS. 2A, 2B and 2C. The device 800 comprises a first portion 802 and a second portion 804 coupled by a flexible link 806.

The first portion 802 is in the shape of an isosceles trapezoid or arrow head and comprises a pair of fixing points 808a, 808b located at the base (large parallel side) of the trapezoid for securing the first portion 802 to a first region of bone, and a securing point 810 located at the short parallel size of the trapezoid (or point of the arrow head) of the first portion for coupling the flexible link 806 thereto. As with the device 200 shown in FIG. 2, first portion 802 may be contoured to match the surface of the first portion of bone to which the first portion 802 is to be secured. In some embodiments, the narrow portion of the first portion 802 where the securing point 810 is provided may bent away from the surface of the bone to avoid the first portion 802 from interfering with the growth plate. In other embodiments, the first portion 802 and/or the second portion 804 may contour closer to the bone to reduce irritation to tissue surrounding the device 800. Preferably, the first portion 802 and/or the second portion 804 are contoured to protect the region between the first and second regions of bone.

The second portion 804 comprises a fixing point 812 for securing the second portion 704 to a second region of bone as well as a securing point 814 for coupling the flexible link 806 to the second portion 804. The securing point 810 of the first portion 802 and/or the securing point 814 of the second portion 804 may each comprise an elongate aperture enabling the flexible link 806 to slide along the length of the aperture during relative movement of the first and second portions 802, 804.

As with the device 200 of FIGS. 2A to 2C, the first portion 802, the second portion 804 or both may be malleable such that during surgery, a clinician is able to mould the device 800 to conform with the bone to which it is to be attached to and to ensure the device 800 does not interfere with the growth plate or other tissue around the bone.

The flexible link 806 may comprise one or more bands, loops, chains, tapes, strings, ropes, wires or the sutures and may be manufactured from the same materials as described above in respect of the flexible link 206 of the device 200 shown in FIGS. 2A to 2C. The flexible link 806 may also be continuous, forming a loop between the securing point 810 of the first portion 802 and the securing point 814 of the second portion 804.

The arrow shaped device 800 is advantageous in that it provides an indication to a surgeon as to which way the first portion 802 is to be mounted relative to the first bone region, i.e. with the arrow pointing towards a growth plate of the bone region.

Figure 9:
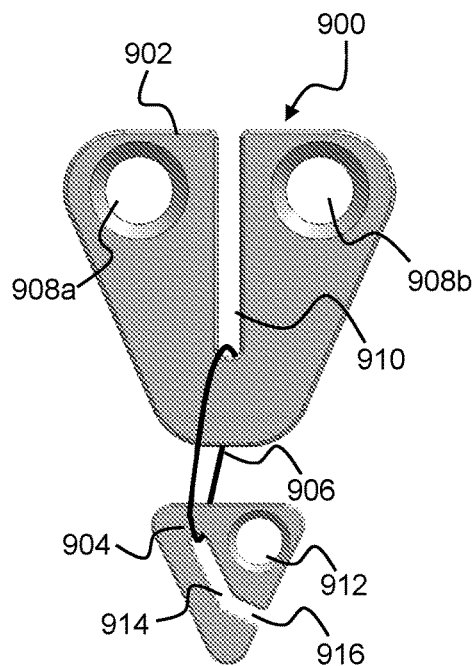
FIG. 9 schematically illustrates an orthopaedic device according to an embodiment of the present disclosure.

FIG. 9 shows another orthopaedic device 900 which is a variation of the device 800 shown in FIG. 8. The device 900 comprises a first portion 902 and a second portion 904 coupled by a flexible link 906.

Like the first portion of the device 800 of FIG. 8, the first portion 902 is in the shape of an isosceles trapezoid or arrow head and comprises a pair of fixing points 908a, 908b located at the base (large parallel side) of the trapezoid for securing the first portion 902 to a first region of bone. The first portion 902 further comprises a securing slot 910 extending from a long edge of the first portion 902 towards the point of the arrow head for coupling the flexible link 906 thereto. As with the device 800 shown in FIG. 8, first portion 902 may be contoured to match the surface of the first portion of bone to which the first portion 902 is to be secured. In some embodiments, the narrow portion of the first portion 902 where the securing point 910 is provided may bent away from the surface of the bone to avoid the first portion 902 from interfering with the growth plate. In other embodiments, the first portion 902 and/or the second portion 904 may contour closer to the bone to reduce irritation to tissue surrounding the device 900. Preferably, the first portion 902 and/or the second portion 904 are contoured to protect the region between the first and second regions of bone.

The second portion 904 comprises a fixing point 912 for securing the second portion 904 to a second region of bone as well as a securing slot 914 for coupling the flexible link 906 to the second portion 804. The securing slot 810 of the first portion 802 and/or the securing slot 814 of the second portion 804 may enable a continuous loop embodiment of the flexible link 906 (shown in FIG. 9) to be looped therein during surgery, thereby enabling the first and second portions 902, 904 to be fitted independently of each other. The securing slot 914 in the second portion 904 is provided with a kink 816 to reduce the likelihood of the flexible link 906 falling out of the securing slot 814 during relative movement of the first and second portions 902, 904 in situ or during movement of tissue over the device 900.

As with the device 200 of FIGS. 2A to 2C, the first portion 902, the second portion 904 or both may be malleable such that during surgery, a clinician is able to mould the device 900 to conform with the bone to which it is to be attached to and to ensure the device 900 does not interfere with the growth plate or other tissue around the bone.

The flexible link 906 may comprise one or more bands, loops, chains, tapes, strings, ropes, wires or the sutures and may be manufactured from the same materials as described above in respect of the flexible link 206 of the device 200 shown in FIGS. 2A to 2C. The flexible link 906 may also be continuous, forming a loop configured to loop over the securing slot 910 of the first portion 902 and the securing slot 914 of the second portion 904.

Figure 10:
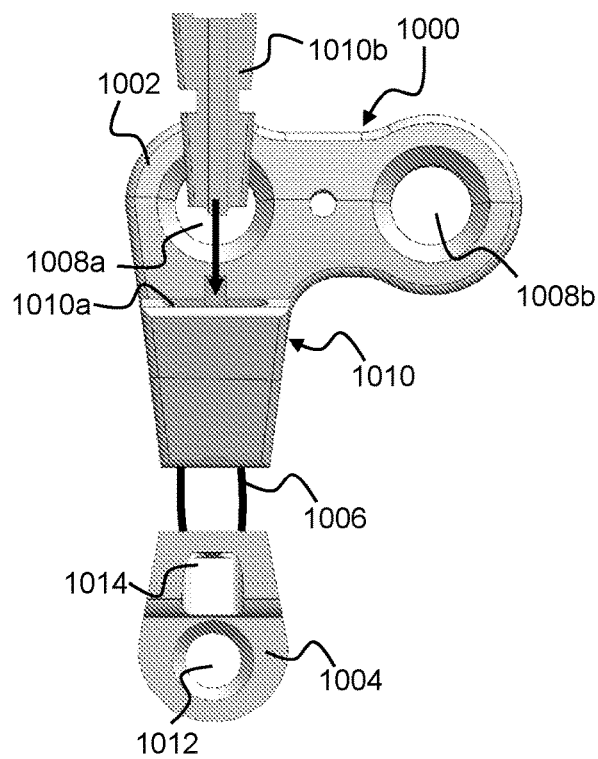
FIG. 10 schematically illustrates an orthopaedic device according to an embodiment of the present disclosure.

FIG. 10 shows another orthopaedic device 1000 which is a variation of the device 700 shown in FIGS. 7A, 7B and 7C. The device 1000 comprises a first portion 1002 and a second portion 1004 coupled by a flexible link 1006.

Like the first portion of the device 700 of FIGS. 7A, 7B and 7C, the first portion 1002 is in the shape of an (inverted) L-plate and comprises a pair of fixing points 1008a, 1008b located at a proximate end (base of the inverted L) for securing the first portion 1002 to a first region of bone. In contrast to the device 700, the device 1000 comprises a securing mechanism 1010 at the base of the inverted L for coupling the flexible link 1006 thereto. The securing mechanism 1010 comprises an aperture configured to receive the flexible link 1006 from a distal end of the device 1000 and a locking pin 1010b configured to lock a portion of the flexible link 1006 within the aperture. In use, the locking pin 1010b may be pushed into a proximate end of the aperture 1010a as denoted by the black vertical arrow in FIG. 10 so as to create an interference fit holding the flexible link 1006 within the aperture 1010a between a surface of the locking pin 1010b and an internal wall of the aperture 1010a.

As with the device 700 shown in FIG. 7, first portion 1002 may be contoured to match the surface of the first portion of bone to which the first portion 1002 is to be secured. In some embodiments, vertical of the T of the first portion 1002 may bent away from the surface of the bone to avoid the first portion 1002 from interfering with the growth plate. In other embodiments, the first portion 1002 and/or the second portion 1004 may contour closer to the bone to reduce irritation to tissue surrounding the device 1000. Preferably, the first portion 1002 and/or the second portion 1004 are contoured to protect the region between the first and second regions of bone.

The second portion 1004 comprises a fixing point 1012 for securing the second portion 1004 to a second region of bone as well as a securing mechanism 1014 for coupling the flexible link 1006 to the second portion 1004 in a similar manner to the securing mechanism 1014 of the first portion 1002 using a pin or the like (not shown) similar to the locking pin 1010b.

As with the device 700 of FIGS. 7A to 7C, the first portion 1002, the second portion 1004 of the device 1000 or both may be malleable such that during surgery, a clinician is able to mould the device 1000 to conform with the bone to which it is to be attached to and to ensure the device 1000 does not interfere with the growth plate or other tissue around the bone.

The device 1000 may be used with a flexible link comprising one or more bands, loops, chains, tapes, strings, ropes, wires or the sutures and may be manufactured from the same materials as described above in respect of the flexible link 206 of the device 200 shown in FIGS. 2A to 2C. The flexible link may also be continuous, forming a loop.

Figure 11:
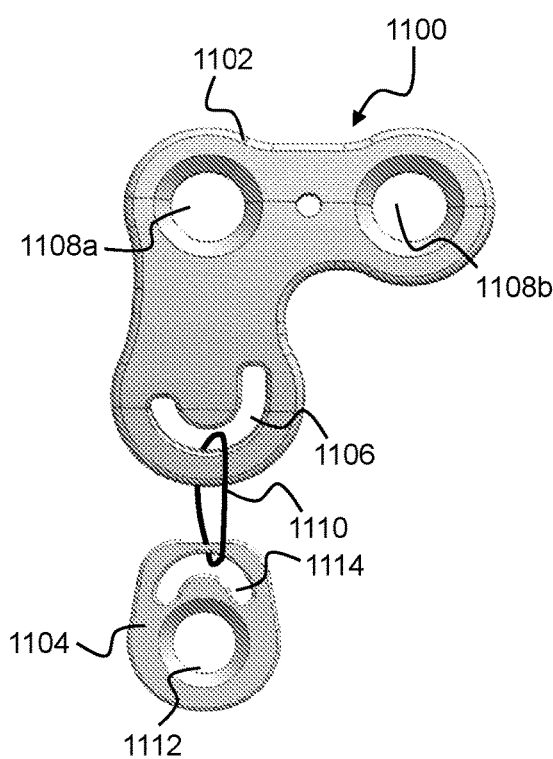
FIG. 11 schematically illustrates an orthopaedic device according to an embodiment of the present disclosure.

A variation of the device 1000 shown in FIG. 10 is shown in FIG. 11. An L-shaped device 1100 is provided comprising a first portion 1102 and a second portion 1104 coupled by a flexible link 1106, and a pair of fixing points 1108a, 1108b for securing the first portion 1002 to a first region of bone. In contrast to the device 1000 of FIG. 10, in place of the securing mechanism 1010, the device 1100 a curved securing slot 1106 is provided in the first portion 1102 for coupling the flexible link 1106 thereto. The curved securing slot 1106 forms an arc which extending through an angular range of rotation enabling the flexible link 1106 to slide and thus hinge about a point centred at the distal end of the first portion 1102 of the device 1100. The curved securing slop 1106 may extend through an expected range of rotation of the flexible link 1110 relative to the first portion 1102. The second portion 1104 may also be provided with a curved securing slot 1114 similar to the slot 1106 of the first portion. The second portion 1004 also comprises a fixing point 1012 for securing the second portion 1004 to a second region of bone.

As with the device 1000 shown in FIG. 10, the first portion 1102 may be contoured to match the surface of the first portion of bone to which the first portion 1102 is to be secured. In some embodiments, the vertical of the L of the first portion 1102 may bent away from the surface of the bone to avoid the first portion 1102 from interfering with the growth plate. In other embodiments, the first portion 1102 and/or the second portion 1104 may contour closer to the bone to reduce irritation to tissue surrounding the device 1100. Preferably, the first portion 1102 and/or the second portion 1104 are contoured to protect the region between the first and second regions of bone.

The first portion 1102, the second portion 1104 or both may be malleable such that during surgery, a clinician is able to mould the device 1100 to conform with the bone to which it is to be attached to and to ensure the device 1100 does not interfere with the growth plate or other tissue around the bone.

It will be appreciated that where possible, any of the first portions of the orthopaedic devices described above may be used with any of the second portions of the orthopaedic devices described above. Further any aspects or features of any of the device described may be re-arranged in any conceivable arrangement while not departing from the scope of the disclosure.

Use of the orthopaedic devices 200, 300, 500, 600, 700, 800, 900, 1000, 1100 has been described in relation to correcting rotational deformities across a growth plate of a bone. However, the present disclosure is not limited to such corrections. For example, instead of securing the device 200 (or any of the other devices described) across a growth plate, the device 200 may equally be used to correct a rotational deformity across a intervertebral disc. FIGS. 12A and 12B show the orthopaedic device 200 described above with reference to FIGS. 2A and 2B attached between a first vertebra 1202 and a second vertebra 1204 separated by an intervertebral disc 1204. FIG. 12A shows the device 200 at the time of securing to the vertebrae 1202, 1204. The first portion 202 of the device 200 is secured at a posterior location on the first vertebra 1202 and the second portion 204 is secured at an anterior location on the second vertebra 1204. The anterior and posterior fixation sites are laterally offset relative to the longitudinal axis of the spine.

As the spine grows in a direction parallel to the longitudinal axis of the spine, tension in the flexible link 206 imparts a torque on the first vertebra 1202 relative to the second vertebra 1204 which in turn causes the first vertebra 1202 to rotate relative to the second vertebra 1204 until, as shown in FIG. 3B, the first and second portions 202, 204 are substantially aligned with one another in a direction parallel to the longitudinal axis of the spine.

Each of the other orthopaedic devices 300, 500, 600, 700, 800, 900, 1000, 1100 described above may be used in a similar manner to the device 200 described in FIGS. 2A and 2B for rotational correction of the spine as described with reference to FIGS. 12A and 12B.

As noted in above with reference to FIGS. 3A and 3B, the devices described herein achieve more elongation per degree of rotation as compared to the prior art device 100 shown in FIGS. 1A and 1B. In addition, the inventors have found that the relative position of implantation of the first and second portions of the devices 300, 500, 600, 700, 800, 900, 1000, 1100 affects the efficacy of treatment. Specifically, the inventors have identified several variable that can be adjusted to improve the orthopaedic correction provided. These will be described with reference to FIG. 13 which shows the orthopaedic device 1100 described above. Using the same notation as that used above with reference to FIGS. 3A and 3B, FIG. 13 shows the initial placement of the first and second portions 1102, 1104 of the device 1100.

Figure 14:
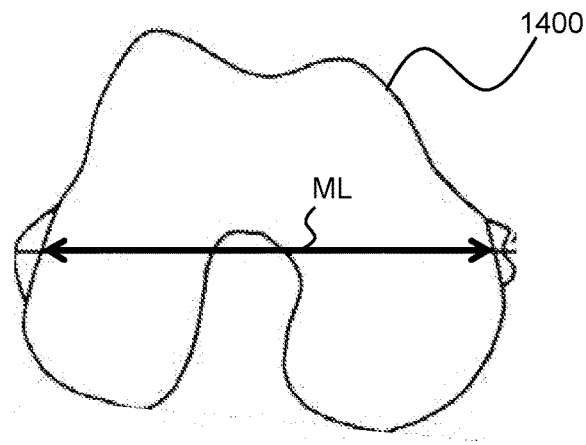
FIG. 14 is a transverse view of a distal femur showing a medial lateral distance (ML)

The angle made between the horizontal and the plane intersecting the rotational centres of the first and second portions 1102, 1104 about which the flexible link 1106 pivots (points B and E) will be referred to here as the initial device angle (IDA). The inventors have found that the initial device angle can be adjusted to increase the linearity in the rate of corrective rotation of the first and second bone portions. The inventors have also found that the initial distance between the first and second portions 1102, 1104 affects the linearity in the rate of relative rotation of the first and second bone portions. This linearity is dependent on, for example, the distance L between the rotational centres of the first and second portions 1102, 1104 about which the flexible link 1106 pivots (points B and E). Referring to FIG. 14, the inventors have further found that the size of the bone being corrected should also be taken into account when determining the distance between points B and E for initial implantation. Taking the femur as an example, FIG. 14 is a transverse view of a distal femur 1400. The distance medial lateral span ML can be used as an indicator of the size of the femur.

Figure 15:
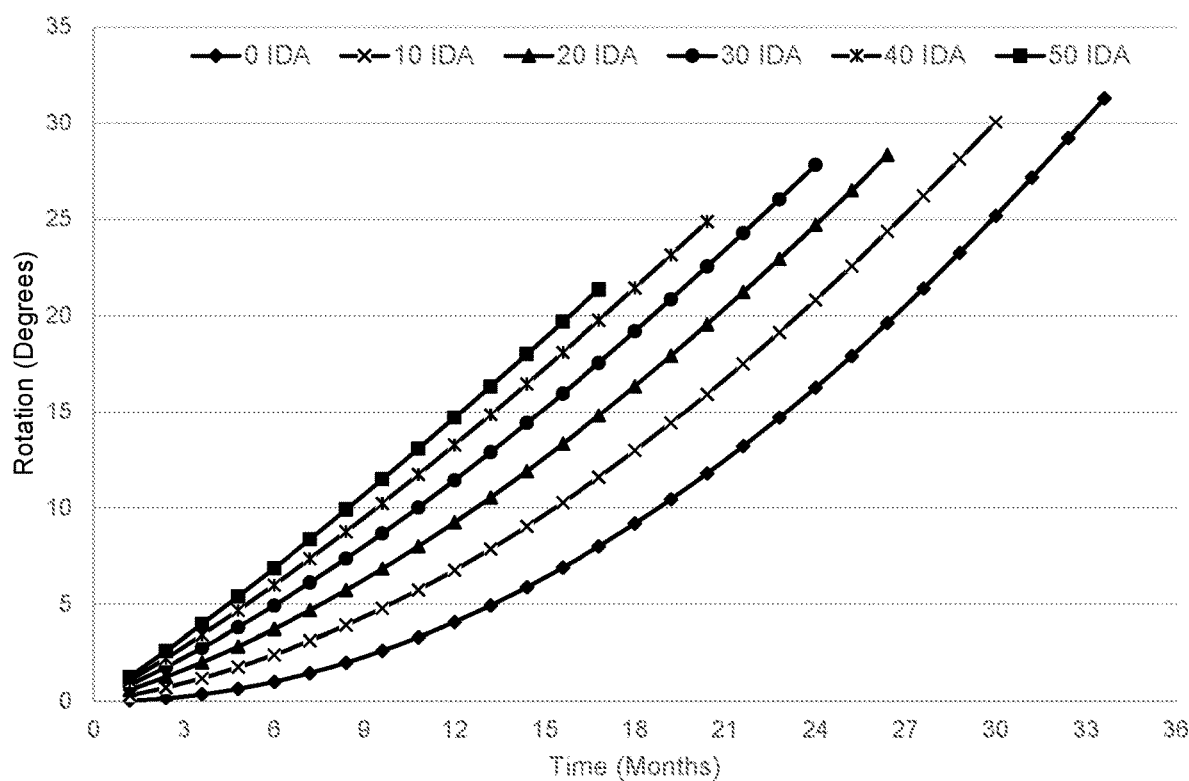
FIG. 15 is a graph illustrating modelled relative rotation of first and second bone portions (y-axis) over time (x-axis) for different initial device angles.

FIG. 15 is a graph illustrating modelled relative rotation of first and second bone portions (y-axis) over time (x-axis) for different initial device angles of 0°, 10°, 20°, 30°, 40°, and 50°, for the device 1100 implanted over a femoral growth plate at a distance BE (L) of 20 mm and in a patient with ML of 70 mm. It can be seen that with an IDA of 0°, the rate of rotation of the first and second bone portions changes considerably over time. Further, for the first 6 months of implantation of the device 1100, the device 1100 provides less than 2° of corrective rotation. In contrast, implanting the device 1100 with an IDA of 50° provides a very linear rate of corrective rotation. However, the device 1100 is limited to providing a total rotation of around 22°. Additionally, the rate of rotation with an IDA of 50° is relatively high which may place too much strain on the growth plate. An IDA of 30° can be seen to provide a relatively linear rate of rotation over a period of about 24 months with a total rotational correction of around 28°. As such, preferably the device 1100 may be implanted with an IDA above 0°, or above 10°, or above 20°, more preferably about 25°. Additionally, the device 1100 may be implanted with an IDA of below 50°, or below 40°, preferably below 35°. In some embodiments, the IDA may be chosen to be between 20° and 40° or between 25° and 35°, preferably about 30°.

Figure 16:
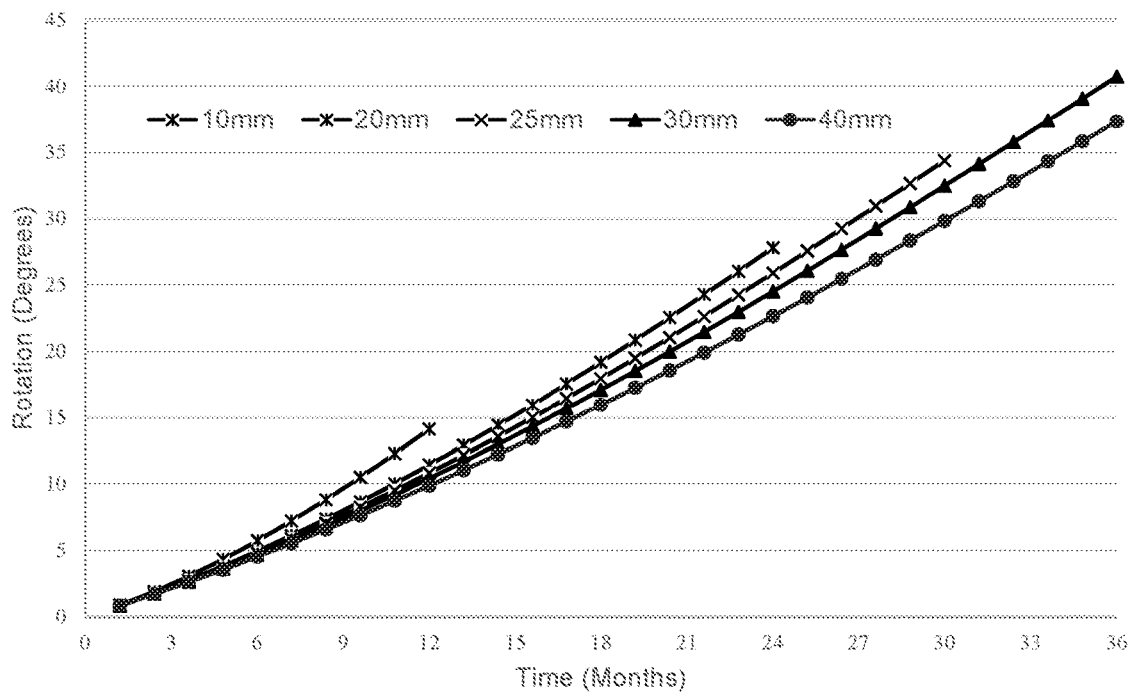
FIG. 16 is a graph showing relative rotation of first and second bone portions over time for different offset lengths (L) of first and second portions.

As illustrated in FIG. 16, it has also been found that the greater the offset L between the first and second portions 1102, 1104 of the device 1100, the more linear the rate of rotation. FIG. 16 shows relative rotation over time for an IDA of 30° implanted in a patient having an ML of 70 mm. It has been found that a distance L of 25 mm provides a linear rate of rotation over a 24 month growth period. Accordingly, in some embodiments, the distance L at which the device 1100 is implanted may be between 20 and 30 mm for example around 25 mm.

Figure 17:
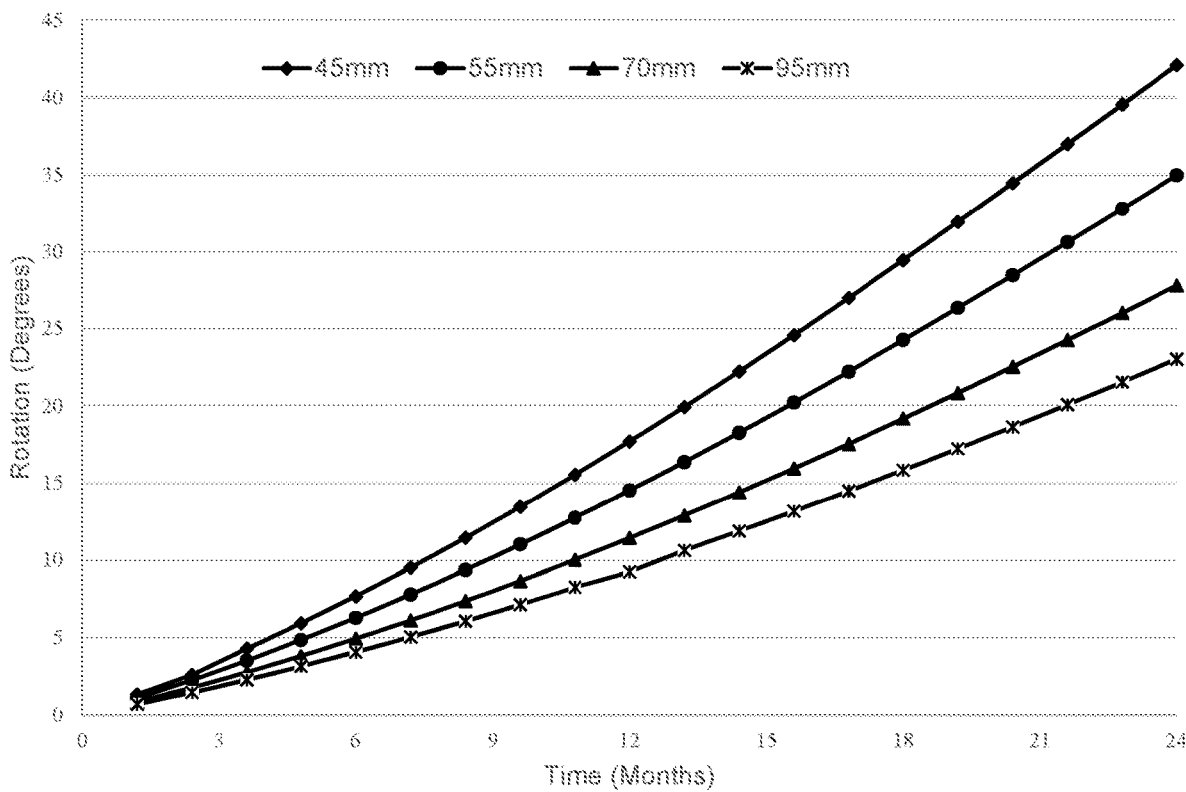
FIG. 17 is a graph showing relative rotation rate for different sized femurs fitted with the device shown in FIG. 11.

It has also been found that the rate of corrective rotation increases with smaller ML distance. This is illustrated in FIG. 17 which shows the rate of rotation for the device 1100 implanted with an IDA of 30° and distance L of 20 mm in patients having ML distance of 45 mm, 55 mm, 65 mm and 75 mm.

Having regard for the above, there is a need during surgery to accurately set the IDA and distance L during implantation of the devices described herein. The inventors have devised a surgical guide which enables such accurate positioning and fixing of first and second portions of one or more of the devices 300, 500, 600, 700, 800, 900, 1000, 1100 to a patient, e.g. across a growth plate.

Figure 18A:
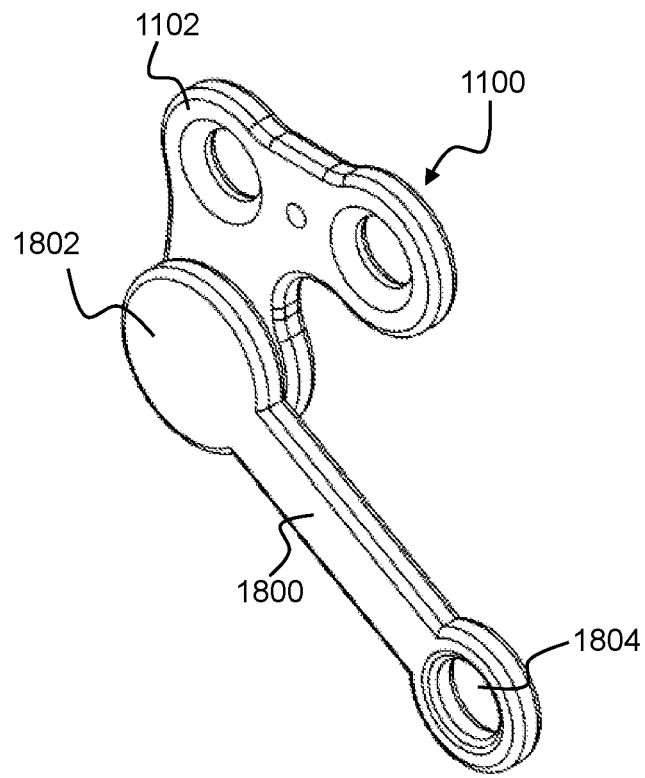
FIGS. 18a and 18b schematically illustrates a surgical guide for use with the device shown in FIG. 11.
Figure 18B:
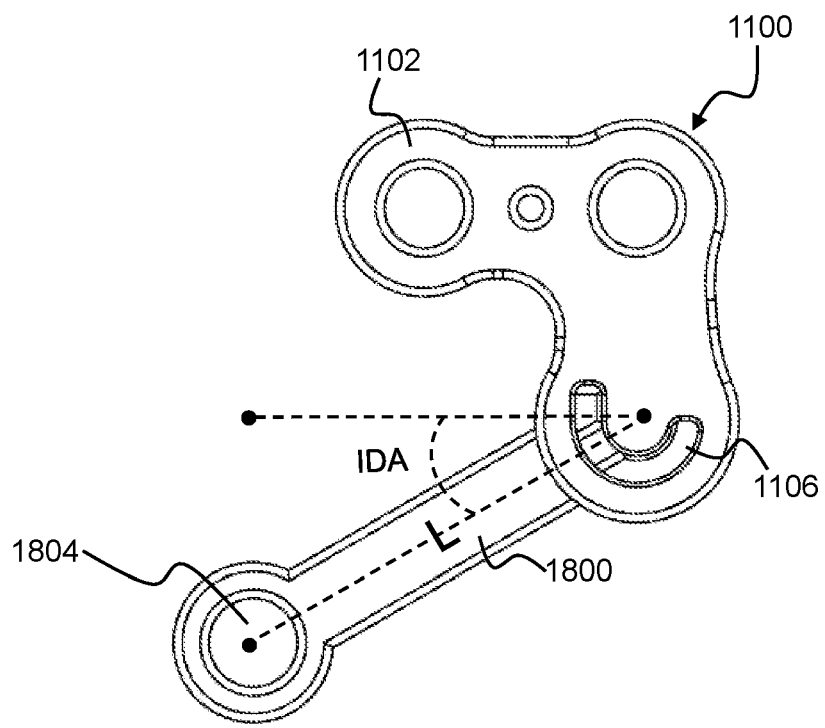

FIGS. 18*a* and 18*b* provide an exemplary surgical guide 1800 which may be used in conjunction with the device 1100 described above with reference to FIGS. 11 and 13. The surgical guide 1800 comprises a mating portion 1802 configured to mate with the securing slot 1106 of the device 1100, for example by means of a curved tongue (not shown). The surgical guide 1800 further comprises a guide hole 1804 separated from the mating portion 1802 by the distance L chosen for the particular embodiment of the device 1100. The mating portion 1802 may mate with the securing slot 1106 in only one angular orientation so that the axis intersecting the guide hole 1804 and the centre of rotation of the slot 1106 forms and the correct IDA relative to the horizontal. This is denoted best in FIG. 18*b* which shows the IDA and distance L with the mating portion matted with the securing slot 1106.

During surgery, the first portion 1102 may be fitted to the first portion of bone. The surgical guide 1800 may be fitted to the first portion 1102 and a fixing location identified on the second portion of the bone for fixing of the second portion 1104 of the device 1100. The second portion 1104 of the device may then be fixe to the second portion 1104 at the positioned indicated by the surgical guide 1800 (e.g. the guide hole 1804).

It will be appreciated that the length and mating angle of the surgical guide 1800 may be chosen to enable the first and second portions 1102, 1104 of the device to be fitted at any relative distance and/or angle depending on the requirements of the specific case.

The surgical guide 1800 may be malleable such that during surgery, a clinician is able to bend the surgical guide 1800 around a bone such that the guide hole 1804 can be brought into proximity with the bone to act as a guide. An intermediate portion 1806 of the surgical guide 1800 separating the mating portion 1802 and the guide hole 1804 may be shaped or manufactured to be more malleable in one direction than another. Taking the embodiments shown in FIG. 18*a* and FIG. 18*b* as an example, the intermediate portion 1806 may be wider than it is thick so that it is able to be deformed around the bone but retains its shape in a direction perpendicular to the bone surface so as to ensure the required IDA is maintained. The surgical guide 1800 may be manufactures from aluminium, lead or similar malleable material.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

What is claimed is:

1. An orthopaedic device for securing between first and second regions of bone separated by a growth plate, the orthopaedic device comprising:
 a first portion comprising at least two fixing points to secure to a first fixing location on the first bone region in a first configuration and a base configured to extend from the fixing points, the base including a securing point;
 a second portion comprising a single fixing point to secure to a second fixing location on the second bone region;
 the first and second portions pivotally coupled to each other around the securing point of the first portion;
 the first portion when secured to the first fixing location and the second portion when secured to the second fixing location being offset relative to each other and to a longitudinal axis of the bone;
 wherein movement of the first and second portions away from each other in a direction parallel to the longitudinal axis of the bone as it grows causes relative rotation of the first and second bone regions, wherein the at least two fixing points of the first portion hold the first portion in the first configuration during growth of the bone.

2. The orthopaedic device of claim 1, wherein movement of the first and second portions away from each other causes the orthopaedic device to move to an extended configuration.

3. The orthopaedic device of claim 2, wherein longitudinal growth of the bone causes the orthopaedic device to move towards the extended configuration.

4. The orthopaedic device of claim 1, wherein the securing point is offset relative to the first fixing location in a direction parallel to the longitudinal axis of the bone and towards the growth plate.

5. The orthopaedic device of claim 1, wherein the second portion comprises one or more second securing points offset relative to the second fixing location in a direction parallel to the longitudinal axis of the bone and towards the growth plate.

6. The orthopaedic device of claim 5, wherein the distance between the first coupling location securing point of the first portion and the one or more second securing points of the second coupling location portion is between 20 and 30 mm.

7. The orthopaedic device of claim 1, wherein the second portion extends at least partially across the growth plate.

8. The orthopaedic device of claim 1, wherein the first portion comprises a T-plate or an L-plate.

9. The orthopaedic device of claim 1, wherein the first and second portions are pivotally coupled by a hinge.

10. The orthopaedic device of claim 9, wherein the hinge is multiaxial.

11. The orthopaedic device of claim 10, wherein the hinge comprises a ball and socket joint.

12. The orthopaedic device of claim 9, wherein the securing point of the first portion is a post which interacts with a slot in the second portion to form the hinge.

13. The orthopaedic device of claim 12, wherein the post is slidable within the slot such that the distance between the second fixing location and a center of rotation of the hinge increases as the first and second portions are moved away from each other.

14. The orthopaedic device of claim 13, further comprising means to limit rotation of the hinge until the distance between the second fixing location and the center of rotation of the hinge reaches a predetermined threshold.

15. The orthopaedic device of claim 14, wherein the base of the first portion extends at least partially across the growth plate.

16. The orthopaedic device of claim 14, wherein the means to limit rotation of the hinge comprises a stop or bevel incorporated into the first portion.

17. The orthopaedic device of claim 1, wherein the first and second portions are pivotally coupled by a flexible link.

18. The orthopaedic device of claim 17, wherein the flexible link comprises one or more bands, loops, chains, tapes, strings, ropes, wires or the sutures.

19. The orthopaedic device of claim 18, wherein the flexible link is manufactured from a material comprising stainless steel, polyester, polymer fibre, polyethylene, ultra-high molecular weight polyethylene (UHMWPE), silk, nylon, polyethylene terephthalate, polytetrafluoroethylene (PTFE), polyurethane, polypropylene, polyvinylidene fluoride, polydioxanone, or a combination thereof.

20. The orthopaedic device of claim 17, wherein the flexible link forms a continuous loop.

21. The orthopaedic device of claim 17, wherein the first portion comprises a first coupling slot for securing the link to the first portion at the securing point.

22. The orthopaedic device of claim 21, wherein the first coupling slot is curved.

23. The orthopaedic device of claim 21, wherein the first coupling slot comprises a first open end for receiving the link.

24. The orthopaedic device of claim 21, wherein the second portion comprises a second coupling slot for securing the link to the second portion at one or more second securing points.

25. The orthopaedic device of claim 24, wherein the second coupling slot is curved.

26. The orthopaedic device of claim 25, wherein the second coupling slot comprises a second open end for receiving the link.

27. The orthopaedic device of claim 1, wherein an inside surface of the first portion is contoured to match a surface of the first bone region and wherein an inside surface of the second portion is contoured to match a surface of the second bone region.

28. A system for correcting rotational deformity of first and second regions of bone separated by a growth plate, the system comprising two or more orthopaedic devices according to claim 1, wherein the two or more orthopaedic devices are arranged around the circumference of the bone spaced equally from one another.

29. A surgical guide for use with the orthopaedic device of claim 1, comprising:
a coupling configured to couple to the first portion of the orthopaedic device of claim 1 in a predetermined relative orientation; and
a surgical indicator configured to identify the second fixing location with the second portion pivotally coupled to the first portion in the predetermined relative orientation.

30. The surgical guide of claim 29, wherein the surgical indicator comprises a guide hole.

31. A method of correcting a bone deformity using the orthopaedic device of claim 1, the method comprising:
securing the first portion of the device to the first location on the first bone region; and
securing the second portion of the device to the second location on the second bone region.

32. The method of claim 31, wherein the first and second portions of the device are secured to the first and second locations such that an initial implantation angle between a first plane perpendicular to the longitudinal axis of the bone and a second plane intersecting the first coupling location and the second coupling location of between 25° and 35°.

33. The method of claim 32, wherein the initial implantation angle is about 30°.

34. The method of claim 31, further comprising:
securing one or more additional orthopaedic devices between the first and second regions of the bone, the orthopaedic device and the one or more additional orthopaedic devices being equally spaced apart around the circumference of the bone so as to impart substantially equal relative rotational force on the first and second bone regions during growth of the bone in a direction parallel to the longitudinal axis of the bone.

35. The method of claim 34, further comprising:
after growth of the bone in a direction parallel to the longitudinal axis of the bone, removing or disabling one or more of the orthopaedic device and the one or more additional orthopaedic devices.

36. The method of claim 31, wherein the bone is selected from the femur, the tibia, the fibula, the humerus, the ulna, or the radius, or wherein the bone comprises a plurality of vertebrae.

37. The method of claim 36 to correct femoral anteversion and antetorsion.

38. The method of claim 37 wherein the first portion is secured to the distal femoral epiphysis and the second portion is fixed to the diaphysis of the distal femur relative to the distal femoral growth plate.

39. The method of claim 38, wherein at least the distal femoral epiphysis is externally rotated relative to the distal femur.

40. A spinal device for securing between a first vertebra and a second vertebra of a spine, the spinal device comprising:
- a first portion comprising at least two fixing points to secure to a first fixing location on the first vertebra in a first configuration and a base configured to extend from the fixing points, the base including a securing point;
- a second portion comprising a single fixing point to secure to a second fixing location on the second vertebra,
- the first and second portions pivotally coupled to each other around the securing point of the first portion;
- the first portion when secured to the first fixing location and the second portion when secured to the second fixing location being offset relative to each other and to a longitudinal axis of the spine;
- wherein movement of the first and second portions away from each other in a direction parallel to the longitudinal axis of the bone as it grows causes relative rotation of the first vertebra and the second vertebra, wherein the at least two fixing points of the first portion hold the first portion in the first configuration during growth of the bone.

41. The spinal device of claim 40, wherein the securing point is offset relative to the first fixing location in a direction parallel to the longitudinal axis of the spine, and wherein the second portion comprises one or more second securing points that are offset relative to the second fixing location in a direction parallel to the longitudinal axis of the spine.

42. The spinal device of claim 41, wherein the first vertebra and the second vertebra are separated by two or more vertebral disc spaces.

43. A guided growth system comprising a plurality of spinal devices according to claim 40.

44. A method of correcting a spinal deformity using the spinal device according to claim 40, the method comprising:
- securing the first portion of the device to the first location on the first vertebra; and
- securing the second portion of the device to the second location on the second vertebra.

* * * * *

UNITED STATES PATENT AND TRADEMARK OFFICE
CERTIFICATE OF CORRECTION

PATENT NO. : 11,890,040 B2
APPLICATION NO. : 17/309454
DATED : February 6, 2024
INVENTOR(S) : David Graham Little et al.

It is certified that error appears in the above-identified patent and that said Letters Patent is hereby corrected as shown below:

In the Specification

In Column 5, Line 7, delete "SC" and insert --5C--.

In the Claims

In Column 17, Claim 6, Line 11, delete "the first coupling location" and insert --the--.

In Column 17, Claim 6, Line 13, delete "second coupling location" and insert --second--.

In Column 18, Claim 34, Line 44, delete "of" and insert --of claim--.

Signed and Sealed this
Tenth Day of September, 2024

Katherine Kelly Vidal
*Director of the United States Patent and Trademark Office*